United States Patent
Reiderman (10) Patent No.: US 7,859,260 B2
(45) Date of Patent: Dec. 28, 2010

(54) NUCLEAR MAGNETIC RESONANCE TOOL USING SWITCHABLE SOURCE OF STATIC MAGNETIC FIELD

(75) Inventor: Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 432 days.

(21) Appl. No.: 11/494,043

(22) Filed: Jul. 27, 2006

(65) Prior Publication Data

US 2006/0255799 A1    Nov. 16, 2006

Related U.S. Application Data

(63) Continuation-in-part of application No. 11/037,488, filed on Jan. 18, 2005.

(51) Int. Cl.
*G01V 3/00*    (2006.01)
(52) U.S. Cl. .................... 324/303; 324/300
(58) Field of Classification Search ........... 324/303, 324/300, 313
See application file for complete search history.

(56) References Cited

U.S. PATENT DOCUMENTS

| | | | | |
|---|---|---|---|---|
| 2,992,389 | A * | 7/1961 | Gondouin | 324/342 |
| 3,453,530 | A | 7/1969 | Attali | |
| 3,538,429 | A | 11/1970 | Baker | 324/0.5 |
| 3,667,035 | A | 5/1972 | Slichter | |
| 3,731,752 | A | 5/1973 | Schad | |
| 3,965,412 | A * | 6/1976 | Yungul | 324/346 |
| 4,035,718 | A | 7/1977 | Chandler | 324/0.5 |
| 4,205,288 | A | 5/1980 | Lin et al. | |
| 4,409,846 | A | 10/1983 | Ueno | |
| 4,465,140 | A | 8/1984 | Hoehn, Jr. | |
| 4,717,878 | A | 1/1988 | Taicher et al. | 324/303 |
| 4,736,634 | A | 4/1988 | Amata | |
| 5,055,787 | A | 10/1991 | Kleinberg et al. | 324/303 |
| 5,086,554 | A | 2/1992 | Murata et al. | |
| 6,002,317 | A | 12/1999 | Pignataro | 335/289 |
| 6,133,735 | A * | 10/2000 | Hurlimann et al. | 324/303 |
| 6,166,543 | A | 12/2000 | Sezginer et al. | 324/303 |
| 6,229,422 | B1 | 5/2001 | Pignataro | 355/289 |
| 6,366,086 | B1 * | 4/2002 | Sen | 324/303 |
| 6,452,388 | B1 | 9/2002 | Reiderman et al. | 324/303 |
| 6,559,640 | B2 * | 5/2003 | Taicher | 324/303 |
| 6,791,331 | B2 | 9/2004 | Conti | |
| 7,046,009 | B2 | 5/2006 | Itskovich | |
| 7,075,298 | B2 * | 7/2006 | Mityushin et al. | 324/303 |
| 7,423,426 | B2 * | 9/2008 | Reiderman | 324/303 |
| 7,463,027 | B2 * | 12/2008 | Prammer et al. | 324/303 |

(Continued)

FOREIGN PATENT DOCUMENTS

GB    2408584 A    6/2005

*Primary Examiner*—Brij B Shrivastav
(74) *Attorney, Agent, or Firm*—Mossman Kumar & Tyler PC (57) ABSTRACT

A nuclear magnetic resonance sensing apparatus and method for operating in an earth borehole comprises a source of switchable magnetic field to polarize nuclei in the region of interest, said source comprising a coil wound on a magnetic core having controllable residual magnetization. Maintaining the magnetization of the core during a polarization interval does not require steady current in the coil. Switching intensity and polarity of magnetization of the core causes precession of spin magnetic moments of the nuclei; the precession induces a signal indicative of nuclear magnetic resonance properties of earth formations.

19 Claims, 9 Drawing Sheets

U.S. PATENT DOCUMENTS

| | | |
|---|---|---|
| 7,663,363 B2 * | 2/2010 | Reiderman ................ 324/303 |
| 2003/0076107 A1 | 4/2003 | Fanini et al. |
| 2003/0129763 A1 | 7/2003 | Chamberlain et al. |
| 2004/0183538 A1 | 9/2004 | Hanstein et al. |
| 2005/0030021 A1 | 2/2005 | Prammer et al. |
| 2005/0189945 A1 | 9/2005 | Reiderman |
| 2006/0255799 A1 | 11/2006 | Reiderman |
| 2007/0222444 A1 * | 9/2007 | Reiderman ................ 324/303 |
| 2009/0015254 A1 * | 1/2009 | Castillo et al. ............ 324/303 |

* cited by examiner

FIG. 10

NUCLEAR MAGNETIC RESONANCE TOOL USING SWITCHABLE SOURCE OF STATIC MAGNETIC FIELD

CROSS-REFERENCE TO RELATED APPLICATIONS

This application is a continuation-in-part of U.S. patent application Ser. No. 11/037,488 filed on Jan. 18, 2005 entitled "Method and Apparatus of Using Magnetic Material with Residual Magnetization in Transient Electromagnetic Measurement" by Arcady Reiderman, which incorporated herein by reference.

BACKGROUND OF THE INVENTION

1. Field of the Invention

The invention relates generally to the field of measuring nuclear magnetic resonance properties of an earth formation traversed by a borehole. More particularly, the invention presents method and apparatus for increasing signal-to-noise ratio and depth of investigation of the nuclear magnetic resonance (NMR) measurements.

2. Background Art

A NMR well logging instrument uses a static magnetic field imposed on an earth formation to align nuclear spin magnetic moments of protons or other nuclei present in the earth formations. The static magnetic field may be naturally generated as in case of using the earth's magnetic field or produced by a permanent magnet or an electromagnet. The aligned spin magnetic moment is brought into excited state either by applying an RF magnetic field or switching the static magnetic field. RF voltages are induced in the receive antenna as a result of precessional rotation of nuclear spin axes of hydrogen protons or other nuclei about the static magnetic field with characteristic resonance or Larmor frequency corresponding to the static magnetic field strength.

Typical NMR tool using precession of the polarized nuclear magnetic moments about the earth's magnetic field comprises a source of static magnetic field polarizing nuclei. The field is turned off to allow free or driven precession about the earth's magnetic field. U.S. Pat. No. 3,538,429 issued to Baker, and U.S. Pat. No. 4,035,718 issued to Chandler give examples of the technique that uses abrupt (non-adiabatic) turning off the static magnetic field and detecting signal generated by free precession of nuclear spin magnetic moments. An improved technique is described in U.S. Pat. No. 3,667,035 issued to Slichter. The polarizing field is terminated adiabatically within a predetermined time interval less than the characteristic thermal relaxation time of the selected nuclei. Prior to the termination an alternated magnetic field directed transversal to the earth's magnetic field at a frequency corresponding to the Larmor precession frequency is applied. As a result of application of the alternating magnetic field and adiabatic termination of the polarizing magnetic field the nuclear spins are sweeping onto condition of driven resonance in the earth's magnetic field. Then the alternating field is abruptly terminated to facilitate free precession of the nuclei in the earth's magnetic field. U.S. Pat. No. 6,366,086 issued to Pabitra addresses an issue of an undesirable signal acquired from borehole fluid. Drawbacks of the methods of this type are poorly defined excitation region as well as relatively low SNR due to power-consumption-limited intensity of switchable static magnetic field.

Another approach to the NMR measurement in the borehole is represented by and U.S. Pat. No. 4,717,878 issued to Taicher et al., U.S. Pat. No. 5,055,787 issued to Kleinberg et al., and U.S. Pat. No. 6,452,388 issued to Reiderman, et al. The approach employs using a permanent magnet that generates polarizing magnetic field that aligns nuclear spin magnetic moment. The angle between the nuclear magnetization is then changed by applying a pulsed radio-frequency (RF) magnetic field at a frequency corresponding to the static magnetic field magnitude at a predetermined distance from the NMR tool. A sequence of RF pulses can be designed to manipulate the nuclear magnetization in order to acquire relaxation property of the earth formation. For the NMR well logging the most common sequence is the CPMG sequence that comprises one excitation pulse and a plurality of refocusing pulses. Due to an extremely inhomogeneous magnetic field the NMR excitation is constrained to a thin shell resulting in relatively shallow region of investigation and sensitivity to any lateral displacement of the logging instrument.

Yet another approach to NMR logging measurement is disclosed in U.S. Pat. No. 6,166,543 issued to Sezginer et al. and U.S. Pat. No. 6,133,753 issued to Hurlimann et al. The approach is based on non-resonant excitation and refocusing and has an advantage of having a relatively large excitation volume compared to resonant excitation methods described above. The method utilizes capability of generating first magnetic field and second magnetic field that is substantially orthogonal to the first magnetic field. Nuclear magnetization is polarized by the first magnetic field. Fast switching between the first and the second magnetic field causes free precession of the nuclear spin magnetic moments about the second magnetic field. A change in polarity of the second magnetic field reverses the direction of precession thereby generating a train of gradient echoes. Practical consideration of power consumption related to fast switching between magnetic fields and maintaining first magnetic field during polarization phase place clear limitations on the strength of the first and the second magnetic fields. The limitations cause relatively low signal-to-noise ratio for measurements at a desired depth of investigation.

Known in the art are electrically or mechanically switchable magnets used in lifting magnetized objects. The magnets do not require a source of constant current. Consequently no energy losses are encountered to maintain magnetization of the magnet. A system representing switchable magnets is disclosed for example in U.S. Pat. No. 6,229,422 issued to Pignataro. The magnet assembly comprises two magnets with coil around one of them. The magnets are typically connected with a magnetically permeable frame. Energizing the coil in one direction reverses the polarization one magnet, thereby effectively short circuiting flux produced by the second magnet. This terminates holding the object. Energizing the coil in the opposite direction causes parallel polarization of the magnets thereby switching the magnet assembly into holding mode. The known in the art switchable magnet systems are not suitable for fast switching the magnetic field. They also unable to provide complete reversal of the magnetic field as well as complete zeroing of the magnetic field.

Thus known in the art instruments do not give a satisfactory solution for effective generating of strong, fast switchable static magnetic field that would facilitate deep and high SNR NMR measurement in downhole environment.

SUMMARY OF THE INVENTION

One embodiment of the invention is a nuclear magnetic resonance (NMR) sensing apparatus for use in a borehole in an earth formation. The apparatus includes a magnetic core with a residual magnetization which polarizes nuclear spins in a specified direction in the earth formation. A coil provides adiabatic deviation of the nuclear spins from the specified direction. A polarizing coil produces a change of a static magnetic field in the specified direction and produces precession of the nuclear spins. A coil detects a signal resulting from the precession of the nuclear spins. The magnetic core may be made of a permeable material having magnetic properties related to a dimension of the core. The magnetic core may further have a coercive force which is substantially equal to the ratio of the saturation magnetization and an effective permeability of the magnetic core in the direction of the magnetic field produced by the polarizing coil. The magnetic material has a substantially rectangular hysteresis loop in the direction of the magnetic field produced by the polarizing coil. The coercive force may be in the range of 1.5-8 kA/m. The magnetic material may be a ferrite, an electrically conducting crystalline magnetic metal ribbon, an electrically conductive magnetic tape and/or an amorphous metal magnetic ribbon. The magnetic material may be a tape or a ribbon with a thickness selected on the basis of a switching time of the magnetic field in the earth formation. The polarizing coil may have an inductance related to a switching time of the magnetic field in the formation.

Another embodiment of the invention is a nuclear magnetic resonance sensing apparatus for use in a borehole in an earth formation. The apparatus includes a magnetic core having a residual magnetization, the core polarizing nuclear spins in a specified direction in the earth formation, the direction being different from a direction of the earth's magnetic field. A polarizing coil carries a current which reduces the magnetic field due to the core to substantially zero. The apparatus includes a receiving coil which receivers a signal resulting from precession of the nuclear spins about the direction of the earth's magnetic field, the precession resulting from the reduction of the magnetic field due to the core. The apparatus may further include an auxiliary coil which substantially eliminates a remainder of the static magnetic field in the earth formation. The apparatus may also include an additional coil which spoils a signal from a fluid in the borehole, the additional coil generating a multi-pole type magnetic field with fast spatial attenuation. The magnetic core may be made of a permeable magnetic material having a magnetic property related to a dimension of the magnetic core. The core material may have a substantially rectangular hysteresis loop in a direction of residual magnetization. The receiving coil may include a multi-turn coil and the polarizing coil may have a small number of coils. The magnetic material may be a ferrite, an electrically conducting crystalline magnetic metal ribbon, an electrically conductive magnetic tape and/or an amorphous metal magnetic ribbon.

Another embodiment of the invention is a method of measuring a nuclear magnetic resonance property in a region of interest of an earth formation. The method includes producing a static magnetic field which polarizes nuclear spins in the region of interest using a source of switchable magnetic field. The source includes a magnetic core having a controllable residual magnetization. The method further comprises inducing and detecting a signal indicative of the NMR property. Inducing the signal may be done by simultaneously switching off the static magnetic field and applying a pulsed magnetic field to provide adiabatic deviation of a direction of polarization of nuclear spins from the direction of the switchable static magnetic filed, replying the static magnetic field, and periodically reversing the polarity of the switchable static magnetic field to generate gradient spin echoes. Inducing the signal may be done by switching off the static magnetic field and generating precession of the nuclear spins around the earth's magnetic field. An auxiliary static magnetic field may be used to correct for a residual inhomogenous magnetic field remaining after switching off the static magnetic field. An additional static magnetic field may be generated to spoil a signal from borehole fluids, the additional static magnetic field being a multi-pole field with fast spatial attenuation.

BRIEF DESCRIPTION OF THE DRAWINGS

This invention is best understood with reference to the accompanying figures in which like numerals refer to like elements and in which.

DETAILED DESCRIPTION OF THE INVENTION

In most general terms, the invention provides an NMR logging tool having a high efficiency source of rapidly switchable static magnetic field. The switchable static magnetic field facilitates NMR measurement in earth's magnetic field as well as an efficient non-resonant excitation of NMR in order to acquire nuclear magnetic resonance properties of earth formations from relatively deep regions in the formations.

Figure 1:
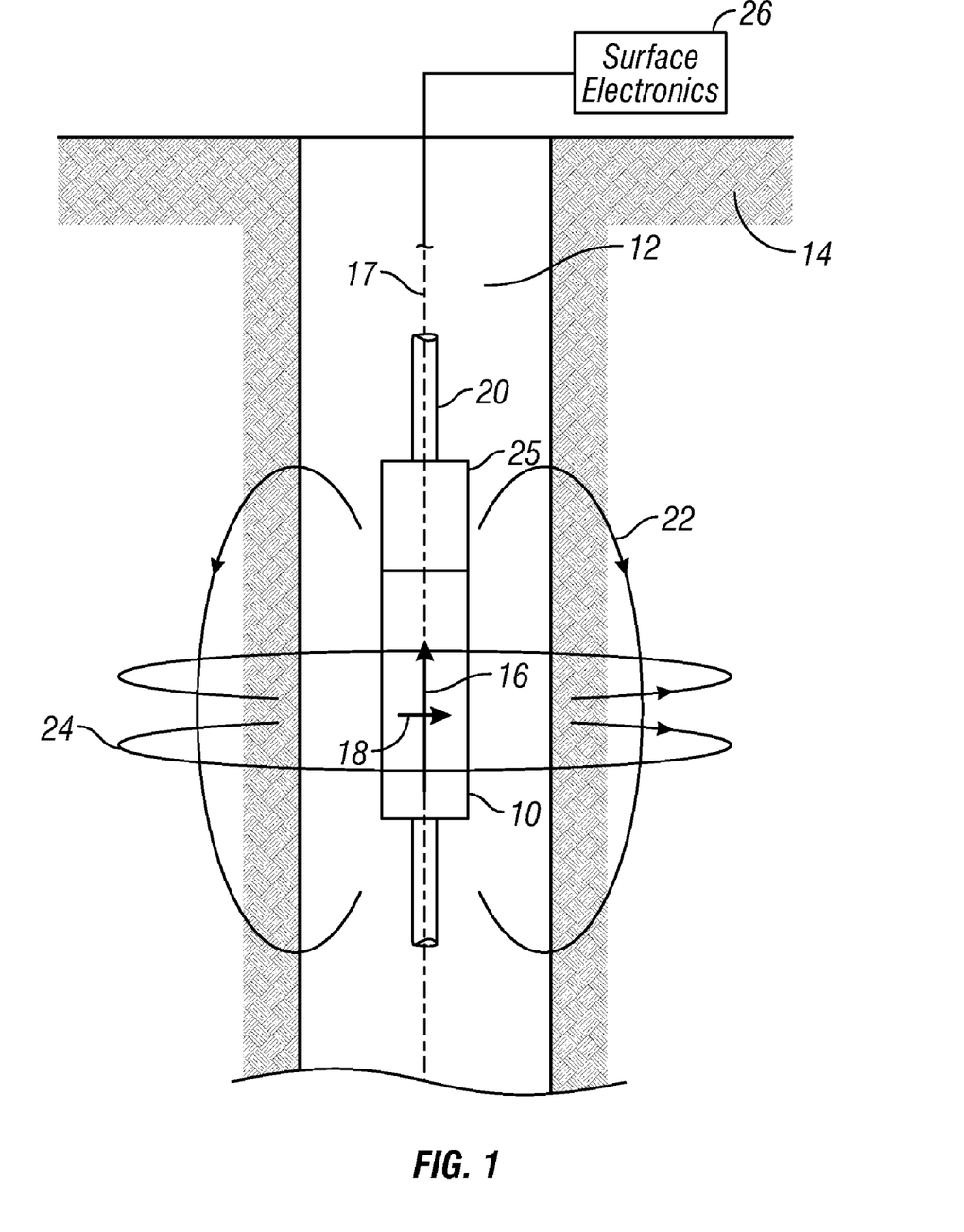
FIG. 1 illustrates a NMR logging system showing directions of magnetic fields with respect to the borehole axis.

FIG. 1 represents an example of a nuclear magnetic sensing apparatus 10 placed in a borehole 12 surrounded by the earth formations 14. The apparatus can be used with an NMR wireline well logging instrument or an NMR instrument for measurement-while-drilling that is conveyed on a drilling tubular. The source of switchable static magnetic field can be a longitudinal dipole 16 directed along the borehole axis 17 or at least one transversal magnetic dipoles 18 in order to energize the earth formations 14. The dipoles typically comprise a magnetic core and a coil wound on the magnetic core. Either dipole can be also used as receiver antenna to receive NMR signal. Separate coils (not shown in FIG. 1) can be also used for receiving NMR signal. Examples of the magnetic flux density lines in the formations 14 surrounding the borehole 12 are shown at 22 and 24 for the longitudinal dipole 16 and a transversal dipole 18 respectively. A part of the source of switchable static magnetic field is a metal support 20 that could be drill collar in case of performing measurements-while-drilling. The nuclear magnetic sensing apparatus further comprises downhole electronics 25 coupled with the coils of the source of switchable static magnetic field and receive coils and a surface electronics 26.

Figure 2:
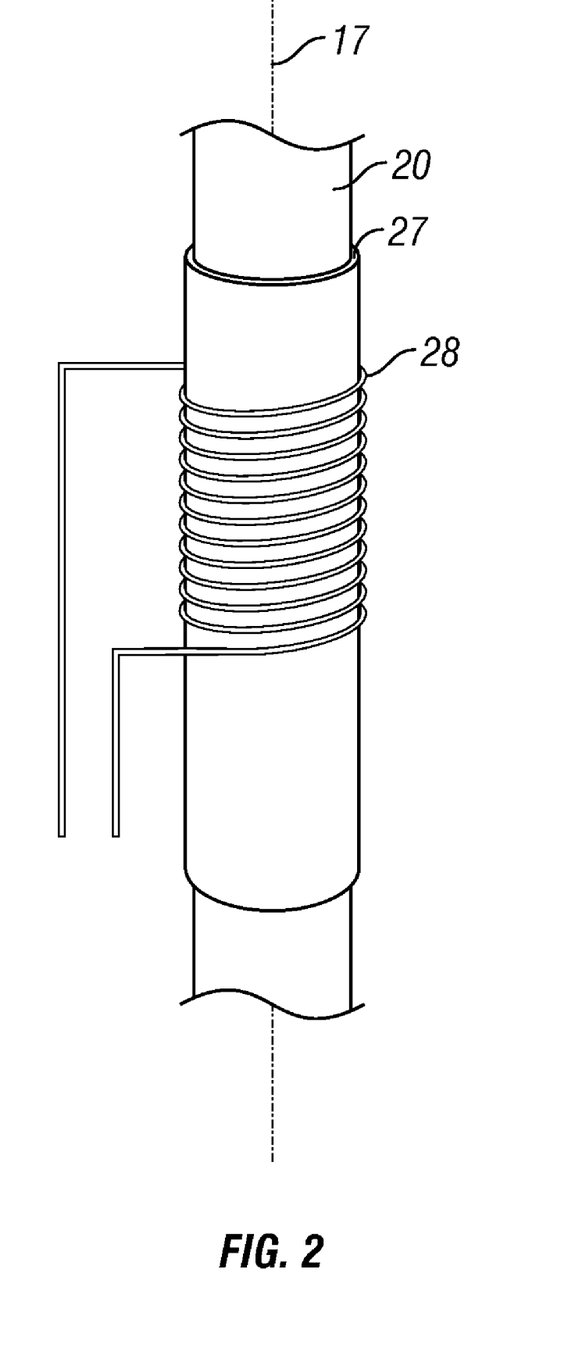
FIG. 2 depicts a simplified layout of a source of switchable static magnetic field having substantially longitudinal orientation using a magnetic core.

Turning now to FIG. 2, a more detailed layout of a simplified source of switchable static magnetic field is presented generating substantially longitudinal magnetic field. The source of switchable static magnetic field comprises a magnetic core 27 surrounding the metal support 20 and a coil 28 that wound around the magnetic core 27. The coil 28 generates magnetic field having direction substantially parallel to the axis 17 that coincides with the axis of the core. Typically the dominant part of the total magnetic flux of the source of the magnetic field is generated due to the core 27. The magnetic core typically ensures that no significant magnetic field passes from the coil 28 to the metal support 20.

Figure 3A:
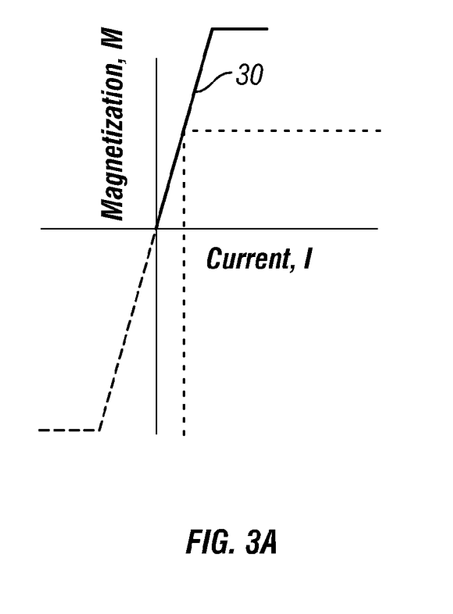
FIG. 3A, FIG. 3B and FIG. 3C show respectively magnetization of the magnetic core versus current in the coil, time diagram of the current in the coil and time diagram of the resultant magnetization of the magnetic core for the source of polarized magnetic field of prior art.
Figure 3B:
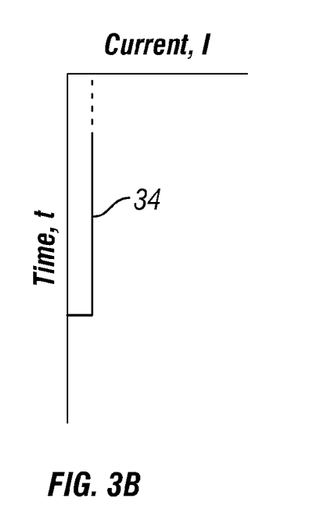
Figure 3C:
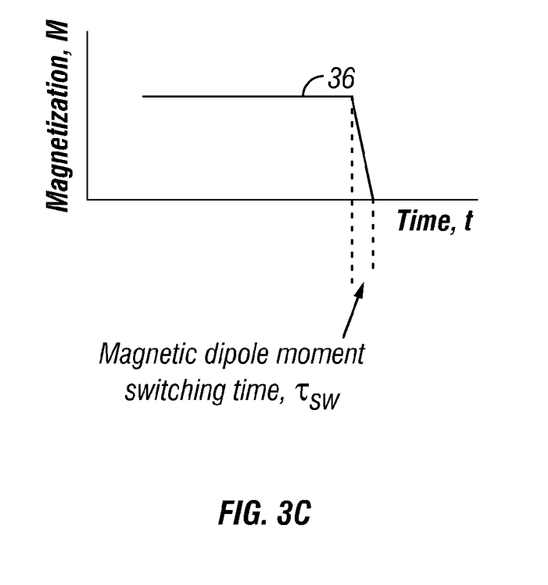

FIG. 3A, FIG. 3B and FIG. 3C show respectively magnetization of the soft magnetic core versus current in the coil 28 (FIG. 2), time diagram of the current in the coil and time diagram of the resultant magnetization of the magnetic core that can represent an embodiment of prior art. The source of switchable static magnetic field known in the art uses conventional high permeability magnetic material with substantially no magnetic hysteresis. A simplified magnetization curve for the magnetic core of prior art is represented by substantially a straight line 30 in FIG. 3A. As will be readily appreciated by those skilled in the art, the slope of the line for a typical high magnetic-permeability magnetic material is mainly determined by the length-to-diameter ratio of the magnetic core. An explanation for this can be found, for example in E. C. Snelling, Soft Ferrites (Properties and Applications), London ILIFE BOOKS LTD or R. M. Bozorth, Ferromagnetism, IEEE PRESS, IEEE Inc, New York. The coil (28 in FIG. 2) is energized with the electric current according to the time diagram in FIG. 3B. In order to perform NMR measurements with non-resonant excitation the current can be supplied in the form of long pulses with relatively short rise and fall time as shown at 34. The switching time of the current limits the frequency of the non-resonant NMR excitation. For the excitation purposes the switching should be fast compared to the Larmor frequency determined by the magnitude of the local static magnetic field. In some practical cases it is desirable for the switching time to be as short as 3-5 μs (Larmor frequency starting from the earth's magnetic field NMR up to 20 kHz) and the duration of the pulse 300-3000 ms. The waveform of the current shown in FIG. 3B causes time variation of the magnetization of the magnetic core shown in FIG. 3C at 36. The magnetic field strength in the surrounding earth formations is proportional to the magnetization presented in FIG. 3C. Accordingly, after the current is turned off, nuclear spins in the earth formation will precess about the earth's magnetic field as long as it is different from the direction of the magnetic filed produced by the magnet. For the magnet configuration in FIG. 2, this direction will be parallel to the longitudinal axis of the tool away from the borehole. This condition is usually satisfied.

As can be seen from the FIGS. 3A, B, C the transmitter antenna of prior art requires that in order to maintain a constant magnetic field in the formation it is required that a constant current flow in the antenna coil. As will be explained below in details the constant current is the main source of power losses related to generation of the magnetic field.

Figure 4A:
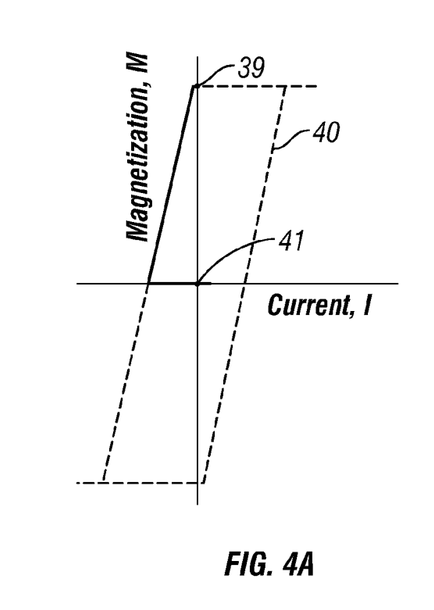
FIG. 4A, FIG. 4B and FIG. 4C show respectively magnetization of the magnetic core versus current in the antenna coil, time diagram of the current in the antenna coil and time diagram of the resultant magnetization of the magnetic core used in an embodiment of logging tool of the present invention.
Figure 4B:
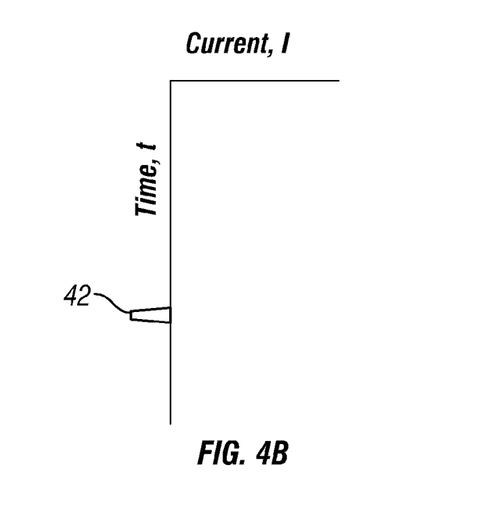
Figure 4C:
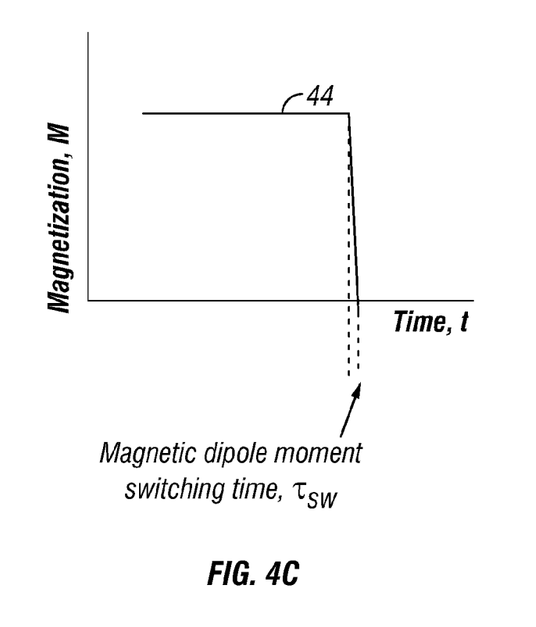

FIG. 4A, FIG. 4B and FIG. 4C show respectively magnetization of the magnetic core versus current in the coil, time diagrams of the current and the resultant magnetization of the magnetic core in accordance with an embodiment of the switchable source of static magnetic field of the present invention. The magnetic core (27 in FIG. 2) is made of a magnetic material having substantial magnetic hysteresis. A simplified major magnetic hysteresis loop representing magnetization and magnetization reversal process in such materials is shown at 40 in FIG. 4A. The waveform of the current driving the coil 28 (FIG. 2) is shown in FIG. 4B at 42. The magnetization states corresponding to the current waveform are represented by the points 39 and 41 on the major hysteresis loop, part of which is shown by solid line in FIG. 4A. Corresponding magnetization waveform is presented in FIG. 4C at 44. As can be seen from the FIGS. 4A, B, and C the current in the coil is present only during switching magnetization in the magnetic core. No current in the coil is required to maintain static magnetic field during polarizing nuclei in the formations. The magnetic core effectively stores magnetic energy in residual magnetization. The energy loss occurs only during switching the magnetization. As will be readily appreciated by those skilled in the art the losses are proportional to the area enclosed in the hysteresis loop corresponding to driving current waveform in the coil 28 (FIG. 2). Since the switching phase of the nuclei polarization cycle is at least 1000 times shorter than the steady-state phase, the power consumption associated with operation of the switchable source of the present invention is much lower that of the prior art.

Factors that put practical limits to the achievable strength of the switchable static magnetic field will be explained below to highlight the advantages of the present invention.

The dipole moment of the magnetic dipole antenna is calculated as follows:

$$p_m = M \cdot s \cdot l \quad (1)$$

where M is the magnetization of the magnetic core 27 (FIG. 2), s and l are respectively the effective cross-sectional area and the length of the magnetic core. A practical assumption is made here of that the main magnetic flux of the antenna is concentrated in the core. The magnetization M for the longitudinal dipole presented in FIG. 2 can be expressed as $$M = \chi_{eff} \cdot H_e = \frac{\chi_{eff} \cdot I \cdot N}{l} \quad (2)$$

where $\chi_{eff}$ is the effective magnetic susceptibility, $H_e$ is the external magnetic field intensity produced by the antenna coil 28; I is the current in the antenna coil during the pulse, l is the effective length of the antenna, and N is the number of turns in the antenna coil.

Then for the magnetic dipole moment we readily get $$p_m = \chi_{eff} \cdot I \cdot N \cdot s \quad (3)$$

The maximum voltage on the antenna coil 28 associated with switching polarity of the magnetic dipole moment is approximately $$V_{max} = L \cdot \left(\frac{dI}{dt}\right)_{max} \approx \frac{2 \cdot I \cdot L}{\tau_{sw}}, \quad (4)$$

where $\tau_{sw}$ is the required switching time, and L is the antenna inductance that can be estimated as follows $$L \approx \mu_0 \cdot \chi_{eff} \frac{N^2 \cdot s}{l}. \quad (5)$$

As can be seen from the equation (4), a short switching time can cause unacceptably high voltage on the coil if the coil inductance is not chosen properly. Assume that the voltage is limited to a certain value $V_{max}$ and the targeted dipole magnetic moment of the antenna and the switching time are respectively $p_m$ and $\tau_{sw}$. Then combining the equation (1)-(5) we readily arrive at the following equation for the current driving the antenna of prior art during the steady-state phase of the formation energizing cycle $$I = \frac{\mu_0 \cdot p_m^2 \cdot}{2 \cdot \chi_{eff} \cdot \tau_{sw} \cdot s \cdot l \cdot V_{max}}. \quad (6)$$

The power losses associated with the current presented by equation (6) are the loss in the antenna coil wire and the loss due to finite conductivity of the electronic switches in conductive state. The first type of losses can be neglected if a large cross-sectional area of the winding (correspondingly heavy coil) is acceptable. The power loss in the switches that may cause overheating the transmitter electronic can be estimated as follows $$P_{loss(prior\_art)} \approx V_{on} \cdot I \quad (7)$$

where $V_{on}$ is on-state voltage of the switch, and I is the current calculated according to equation (6).

As will be shown in the example below the power loss presented by the equations (6) and (7) place clear limit on the achievable target parameters $p_m$ and $\tau_{sw}$ in the methods and apparatuses of prior art.

According to the method of present invention the power losses exist only during switching the polarity of the magnetic dipole of the antenna while during the long steady-state phase the dipole moment is maintained by the residual magnetization of the magnetic core. The losses are caused by the irreversible processes (hysteresis) associated with magnetization reversal in magnetic core. It is well known in the art that energy lost during full cycle of magnetization changes can be presented as the area enclosed in the hysteresis loop in $\mu_0$M-$H_e$ coordinates multiplied by the volume of the core (see for example Chikazumi S, Physics of Magnetism, John Wiley and Sons, New York, 1964). An example of a simplified hysteresis loop with substantial hysteresis is presented in FIG. 4A (magnetic field intensity is proportional to the current in the antenna coil as explained at equation (2)). For the simplified shape of the hysteresis loop presented in FIG. 4A the energy loss due to hysteresis can be expressed as follows $$W_h \approx \mu_0 \cdot 2 \cdot M_s \cdot H_c \cdot s \cdot l \quad (8)$$

where $M_s$ is the saturation magnetization presented in FIG. 4A at 39, $H_c$ is the coercive force defined as the external magnetic field corresponding to zero magnetization on the hysteresis loop of the of the magnetic core. As was explained above, the external magnetic field that causes changes in magnetization of the magnetic core is generated by the current in the antenna coil 28 in FIG. 2.

The energy loss presented by equation (8) is associated with magnetization switching on and off. Then taking into account equation (1) for the magnetic dipole moment the average power loss over the cycle of measurement can be given as follows:

$$P_{loss} = \mu_0 \cdot \frac{2 \cdot p_m \cdot H_c}{T}. \quad (9)$$

where T is the duration the cycle.

In order for the saturation magnetization $M_s$ to be substantially equal to residual magnetization of the core the following two conditions should be met. Firstly, the magnetic material itself should have almost rectangular hysteresis loop when measured in closed magnetic circuit configuration (no magnetic poles). Secondly the following relationship between parameter of hysteresis loop as measured on the core (magnetic poles are located near the ends of the core and create so called demagnetizing field) must hold $$\frac{M_s}{\chi_{effm}} \leq H_c \quad (10)$$

where $\chi_{effm}$ is the maximum effective magnetic susceptibility defined as maximum slope on the ascending or descending parts of magnetic hysteresis loop and the other quantities are the same as in equation (8). As will be readily appreciated by those skilled in the art, said slope is mainly determined by the elongation ratio of the magnetic core, the maximum effective susceptibility can be controlled by varying the elongation ratio. In order to satisfy the inequality (10) the saturation magnetization $M_s$ and coercive force $H_c$ can be also controlled by choosing magnetic materials. Yet another way to get a desired $M_s$ is to make a layered core in which magnetic material is separated by a non-magnetic binding material in order to reduce packing density of magnetic material in the core and correspondingly reduce the net magnetization of the core. Examples of such material are given below. In case maximum possible dipole moment is the main objective in designing the transmitter antenna the product of magnetization and the effective cross-sectional area of the core should be kept possibly high. For a given length of the antenna this would result in high ratio $M_s/\chi_{effm}$ and require material with higher coercive force $H_c$ in order to satisfy the equation (10).

Figure 5:
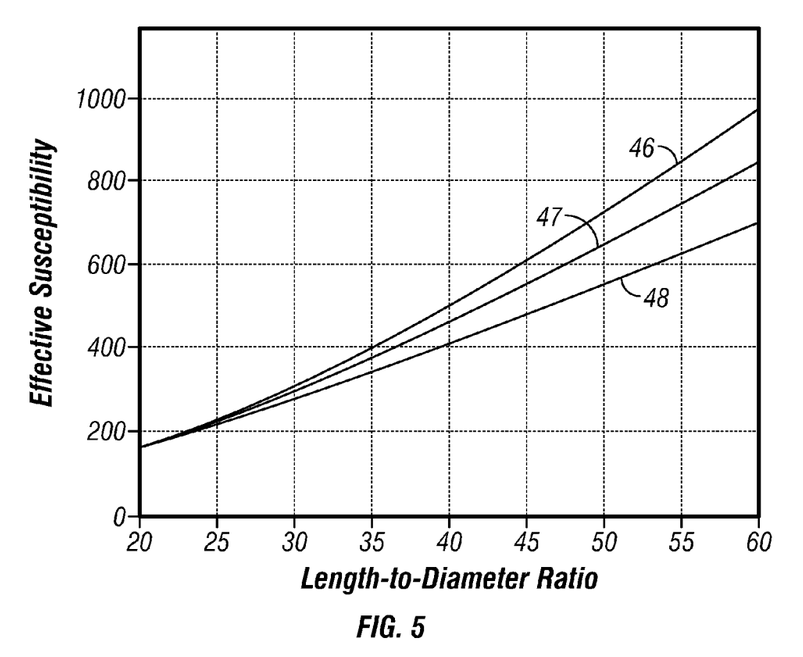
FIG. 5 is a graph showing effective magnetic susceptibility of the magnetic core as a function of the core dimensions.
Figure 6:
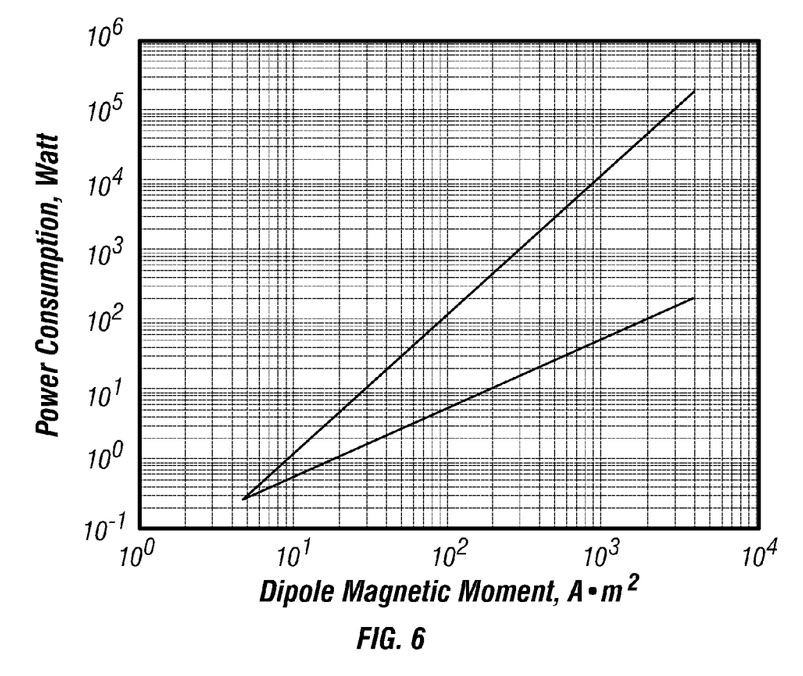
FIG. 6 is a diagram showing power consumption of the source of switchable static magnetic field of FIG. 2 as a function of magnetic dipole moment of the antenna, for the antenna embodiment of the present invention in comparison with that of prior art.

As was mentioned before the effective magnetic susceptibility is primarily determined by the elongation of the magnetic core that is by its geometric parameters s and l. The calculated numbers for rods with different elongation (length-to-diameter ratio) can be found, for example, in E. C. Snelling, Soft Ferrites (Properties and Applications), London ILIFE BOOKS LTD cited above. An example of the dependence of effective susceptibility on length-to-diameter ratio of a magnetic rod is presented in FIG. 5. The curves 46, 47 and 48 in FIG. 5 corresponds to different magnetic susceptibilities of magnetic material of the rod: respectively to 10000, 4000 and 2000. As can be seen in FIG. 6 for a practical range of length-to-diameter ratio of 20-60, the effective susceptibility is 150-800. Then assuming $M_s$=0.8 MA/m (corresponds to the saturation flux density $B_s$=$\mu_0 \cdot M_s$=1T) and using condition described by (10) we determine the following desired range of coercive force: $H_c$=1.5-8 kA/m. The dipole moment corresponding to $M_s$=0.8 MA/m, l=1 m and length-to-diameter ratio equal to 50 is 700 A·m².

The preferable range 1.5-8 kA/m for the coercive force can be achieved for example by using magnetic materials such as rolled permalloy (magnetic properties of this type of materials can be found for example in sited above R. M. Bozorth, Ferromagnetism, IEEE PRESS, IEEE Inc, New York), some amorphous ribbons or some types of ferrites.

FIG. 6 is a diagram showing power consumption as a function of magnetic dipole moment for the longitudinal dipole of FIG. 2. Data for the antenna of prior art in comparison with an embodiment of the present invention are shown at 50 and 52 in FIG. 6. The data was calculated according to equations (6) and (7) for prior art and equation (9) for the present invention. The following practical numbers were used for this example: $\chi_{eff}$=150, $\tau_{sw}$=3 µs, s=0.002 m², l=1 m, $V_{max}$=1000V, $V_{on}$=3.9V (the number for the on-state voltage of the switch is taken from Advanced Power Technology catalog for IGBT type switch APT75GP120B2), $H_c$=1 KA/m, T=100 ms. The effective magnetic susceptibility $x_{eff}$ was taken from the data presented in FIG. 5 at 48 for the length-to-diameter ratio calculated as follows: $l/\sqrt{4 \cdot s/\pi}$. As can be seen in FIG. 6 the power consumption for the source of magnetic field of prior art and of the present invention while similar for small dipole moments (less than 10 A·m²) dramatically differ at larger dipole moments. For example generating the dipole moment of 1000 A·m² would take as much as 10 kW DC power for the source of the prior art and only about 50 W of DC power for the source of magnetic field according to an embodiment of present invention. The greater dipole moment of the transmitter antenna the deeper penetration into earth formations can be achieved. It should be understood from the data presented in FIG. 6 that high power dissipation and heat removal problems make it impractical for methods and apparatuses of prior art to achieve a dipole moment of more than 100 A·m², while dipole moments in excess of 1000 A·m² look quite feasible for the source of switchable magnetic field of present disclosure.

It will be also readily understood by those skilled in the art that for the electro-magnets of prior art it is hard to achieve stability of the dipole magnetic moment because of heating problems. In the present invention the magnetic dipole of the antenna is determined primarily by the magnetization of the magnetic core.

Figure 7:
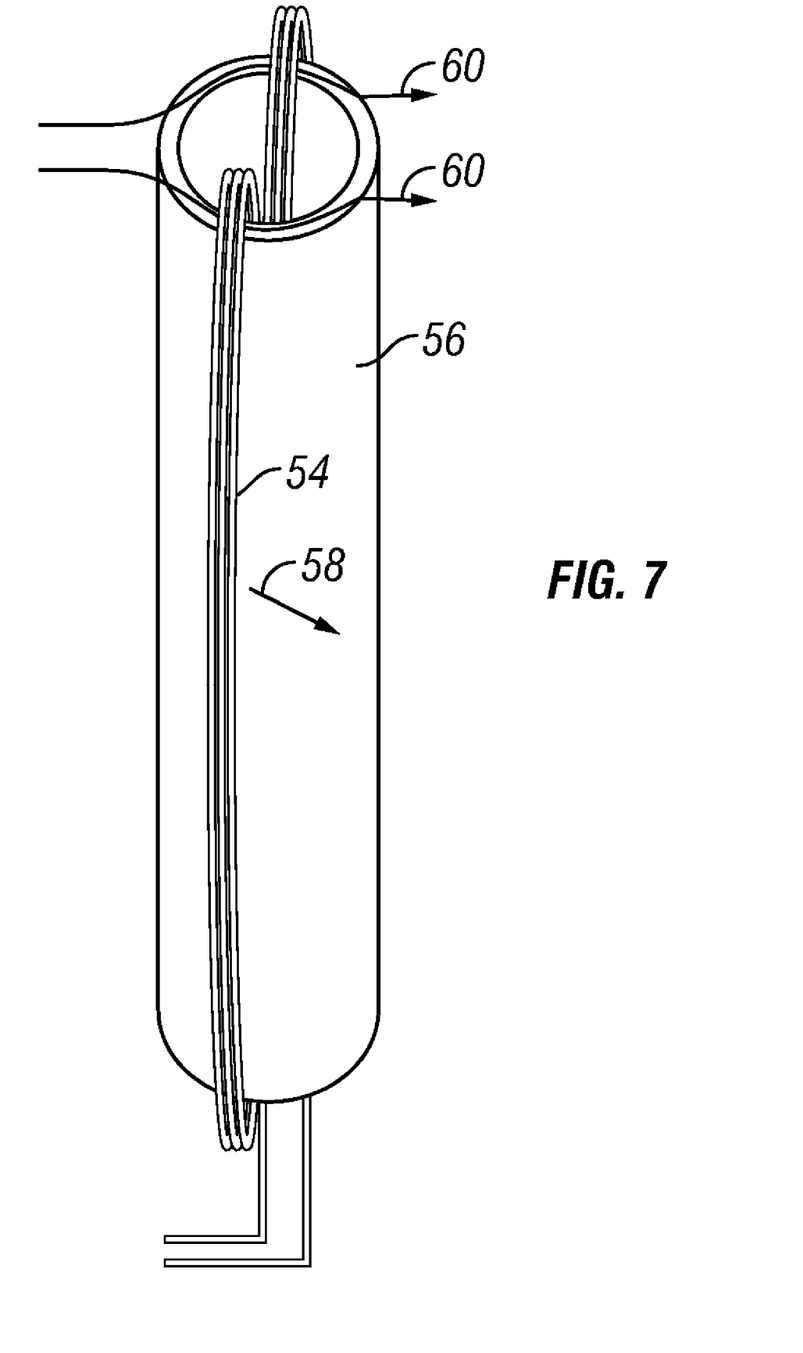
FIG. 7 shows a simplified layout of a magnetic core with the coil for a source of substantially transversal magnetic field in the region of interest.

Reference is now made to FIG. 7 where a transversal magnetic dipole is presented as an embodiment for the switchable source of magnetic field. In some designs the transversal magnetic field could be a preferable configuration for NMR logging instrument implementation. The winding 54 and the magnetic core 56 are arranged to produce magnetic dipole moment 58 directed perpendicularly to the axis of the core (17 in FIG. 2). Two magnetic flux lines are shown at 60 in FIG. 7. It will be readily understood by those skilled in the art that in order to achieve substantial residual magnetization in transversely magnetized magnetic core a higher coercive force of the core material is required as compared to that of the longitudinally magnetized core.

Figure 8:
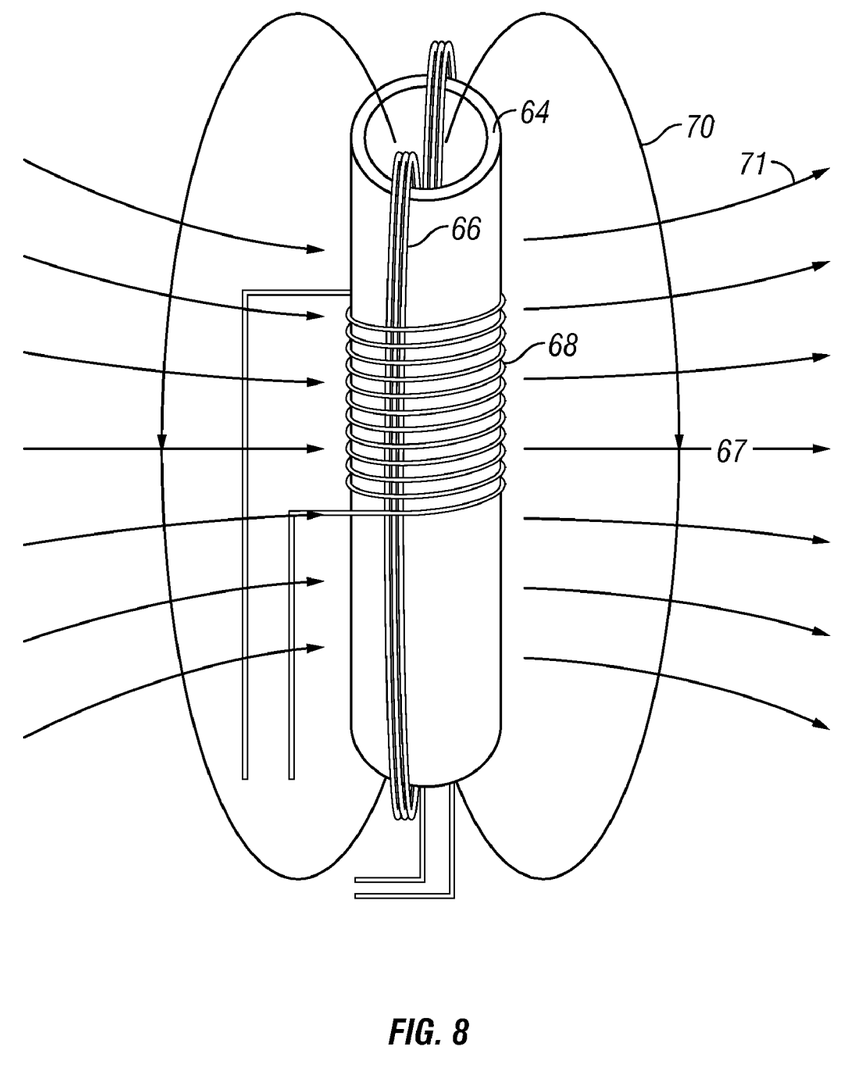
FIG. 8 illustrates an embodiment of present invention that uses non-resonant excitation and gradient echo generation.
Figure 9:
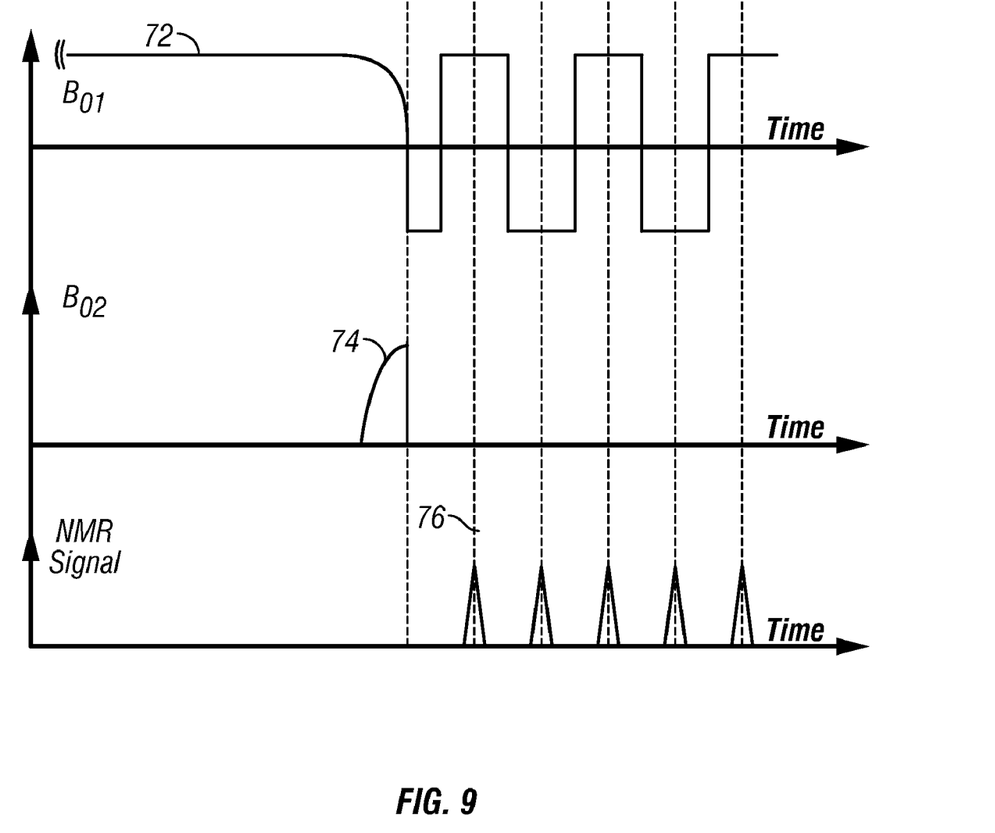
FIG. 9 represents time diagrams of the polarizing and pulsed magnetic field as well as NMR echo signal for the embodiment of FIG. 8.

FIG. 8 represents an embodiment of the present invention. A source of switchable magnetic field provides static magnetic field polarizing nuclear spin magnetic moments in the region of interest 67 in a predetermined direction. The source comprises polarizing coil 68 and magnetic core 64 coupled with the polarizing coil, said magnetic core having residual magnetization to remain magnetized without a steady current in the polarizing coil. A source of pulsed magnetic field presented by the coil 66 and the core 64 provides adiabatic deviation of the direction of polarization of the nuclear spin magnetic moments from said predetermined direction. The flux line of the polarizing magnetic field and the pulsed magnetic field are presented at 70 and 71 respectively. The time diagrams of the polarizing magnetic field $B_{01}$ (at 72) and pulsed magnetic field $B_{02}$ (at 74) are presented in FIG. 9. The initially magnetized core of the source has a polarizing field which polarizes the nuclei in the volume of interest. Then simultaneously two events happen: the polarizing field is switehd off and the pulsed magnetic field is built up. As noted above, the pulsed magnetic field, is orthogonal to the polarizing magnetic field. As a result the magnetization of the nuclei rotates adiabatically by about 90°. The processes of switching off the polarizing field and building up the pulsed field are slow enough to provide adiabatic rotation and fast compared to the relaxation rate of the nuclear magnetization. Then the pulsed magnetic field is switched off abruptly while the polarizing magnetic field builds up opposite polarity with respect to initial direction of polarization. This is referred to as alternations of the magnetization in the direction of intial polarization. This results in generating precession of the nuclear spin magnetic moments about the direction of the polarizing magnetic field. Changing polarity of the polarizing magnetic field generates gradient echoes (at 76 in FIG. 9) in a receiving coil. The coil 66 in FIG. 8 can serve as the receiving coil. Any other coil can be used with sensitivity direction perpendicular to the polarizing magnetic field.

Using pulsed magnetic field in the above described technique can be omitted. In this case the adiabatic removal of the polarizing magnetic field will cause magnetization to align with the earth's magnetic field. Once the polarizing field is non-adiabatically switched on, the magnetization will precess about the polarizing field direction.

Figure 10:
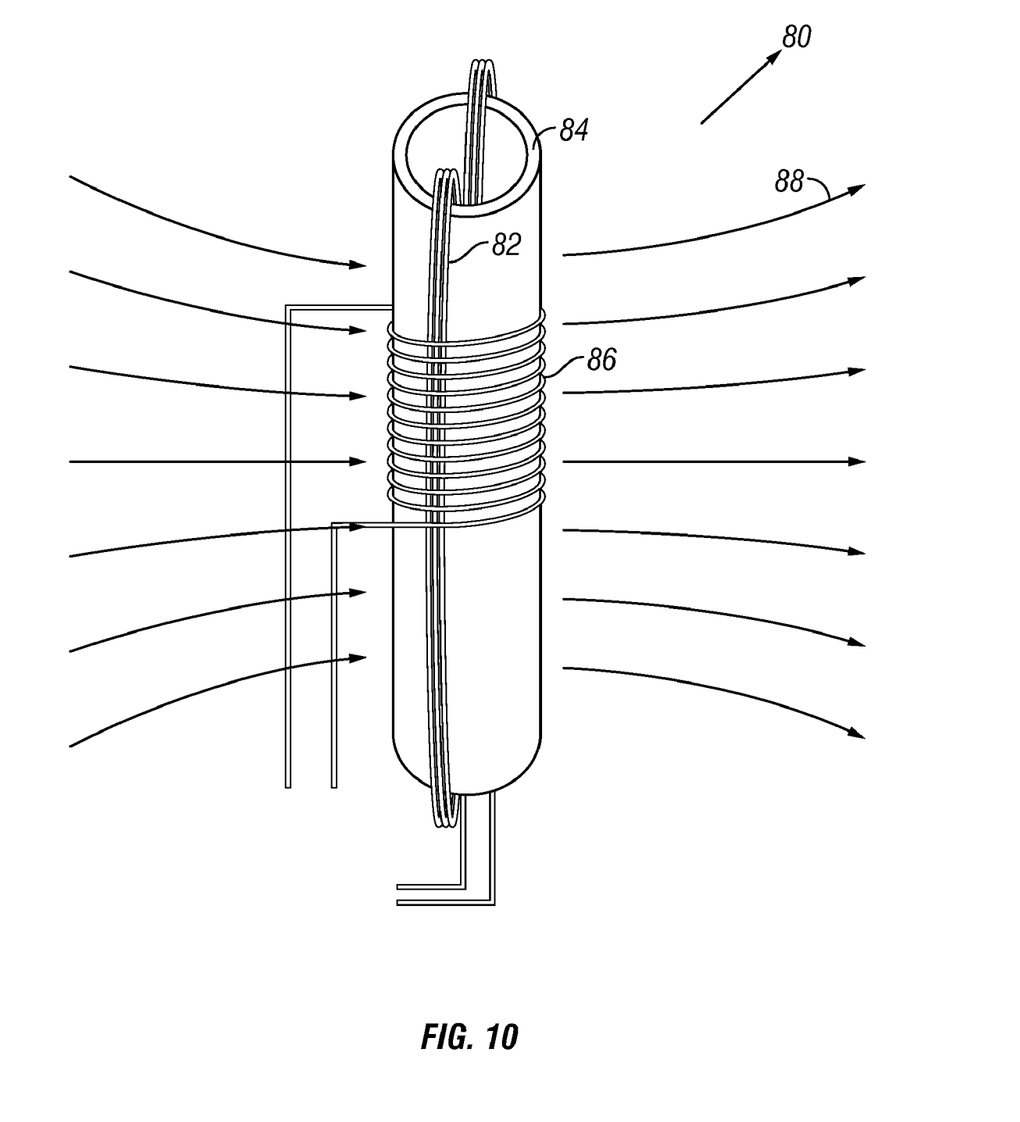
FIG. 10 illustrates an embodiment of present invention that uses earth's magnetic field to generate free precession of the nuclear spin magnetic moments.

FIG. 10 represent another embodiment of the present invention is a nuclear magnetic resonance (NMR) sensing apparatus utilizing earth's magnetic field. The apparatus comprises a source of switchable magnetic field to provide a static magnetic field polarizing nuclei in the region of interest in a direction that is different from the direction of the earth's magnetic field 80. The polarizing source comprises a polarizing coil 82 connected to the source of current and a magnetic core 84 coupled with the polarizing coil. The residual magnetization of the magnetic core is controlled by the magnetic field of the polarizing coil. The polarizing magnetic filed is switched off abruptly (non-adiabatically) to allow for a free precession of the nuclei spin magnetic moments about the earth's magnetic field. The free precession induces an induction signal in the coil 86. The time diagrams of the polarizing magnetic field and the states of magnetization of the magnetic core 84 are the same as shown in FIG. 4.

The polarizing magnetic field direction 88 in the embodiment of FIG. 10 is chosen to be perpendicular to the elongation of the magnetic core. As was explained earlier above the material to be used in this configuration must have higher coercive force than that of the material used in the configuration with longitudinal magnetization. The higher coercive force is accompanied by lower magnetic susceptibility in the reversible part of the hysteresis loop. This will cause less distortion to the homogeneous earth's magnetic field. The undistorted homogeneity in the region of interest is required to ensure that the free precession decay represents nuclear relaxation properties. Some residual magnetization remaining after switching off the polarizing field as well as unwanted magnetization of the core caused by the earth's magnetic field can be eliminated by using orthogonal correcting coils principally of the same configuration as the coils 82, 88. Some residual magnetization of the core may be intentionally left in order to spoil signal from the borehole fluids and from the shallow regions of the formations. In this case an excessive magnetic field due to residual magnetization of the core and magnetic fields of the correcting coils near the tool will result in generating NMR signal at a frequency away from the receiving bandwidth.

The magnetic material that is preferably used for magnetic core is a layered material made of thin tapes of magnetic metal separated with non-conductive layers. The magnetic metal can be, rolled permalloy or magnetic amorphous tape. The core may be assembled from ribbon wound rings or from packs of tapes. The average magnetization of the core depends on the fraction of the magnetic material in the cross-sectional area of the core. The saturation magnetization of the core should preferably obey the condition presented by the equation (10). It should be understood that during switching of the magnetic field of the antenna coil there will be eddy currents generated in magnetic layers. This will cause delay in building up the average magnetization of the core and affect the rate of switching of magnetic dipole of the antenna. To ensure that the delay does not exceed the switching time required to perform transient measurement the magnetic layers must be thin enough. In frequency spectrum terms this means that the thickness should be substantially smaller than the electromagnetic skin depth for the maximum frequency of the spectral band of the transient signal. If, for example, the required switching time is less than 5 microseconds, then the thickness of the magnetic layers should not typically exceed 10 micrometers.

It should be also understood that other magnetic materials can be used in the antenna of the present invention. For example magnetic ferrite materials that are inherently non-conductive can be effectively employed if manufactured to have proper magnetic parameters discussed earlier above.

The operation of the logging tool may be controlled by the downhole processor and/or the surface processor. Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is

1. A nuclear magnetic resonance (NMR) sensing apparatus configured for use in a borehole in an earth formation, the apparatus comprising:
    a magnetic core having a residual magnetization, the magnetic core configured to produce a static magnetic field in a specified direction in the earth formation and polarizing nuclear spins in the specified direction;
    a coil configured to provide adiabatic deviation of the nuclear spins from the specified direction;
    a polarizing coil configured to produce a change of a static magnetic field in the specified direction and configured to produce precession of the nuclear spins about the specified direction; and
    a coil configured to detect a signal resulting from the precession of nuclear spins.

2. The apparatus of claim 1 wherein the magnetic core is made of a permeable magnetic material having a magnetic property related to a dimension of the magnetic core.

3. The apparatus of claim 2 wherein the magnetic core further has a coercive force, which is substantially equal to the ratio of saturation magnetization and an effective permeability of the magnetic core in the direction of the magnetic field produced by the polarizing coil.

4. The apparatus of claim 2 wherein the permeable magnetic material has a substantially rectangular hysteresis loop in the direction of magnetic field produced by the polarizing coil.

5. The apparatus of claim 2 wherein said magnetic material has a coercive force in the range 1.5-8 kA/m.

6. The apparatus claim 2 wherein the permeable magnetic material is selected from the group consisting of (i) a ferrite, (ii) an electrically conductive crystalline magnetic metal ribbon, (iii) an electrically conductive magnetic tape, an (iv) an amorphous magnetic ribbon.

7. The apparatus of claim 6 wherein the magnetic field in the earth formation has a switching time, and wherein the permeable magnetic material comprises at least one of (i) a ribbon, and (ii) a tape having a thickness selected based on the switching time.

8. The apparatus of claim 1 wherein said static magnetic field in the earth formation has a switching time, and the polarizing coil has an inductance related to said switching time.

9. A nuclear magnetic resonance (NMR) sensing apparatus configured for use in a borehole in an earth formation, the apparatus comprising:
    a magnetic core having a residual magnetization and configured to produce a static magnetic field in a specified direction in the earth formation and polarize nuclear spins in the direction, the specified direction being different from a direction of the earth's magnetic field;
    a polarizing coil configured to carry a current which reduces the magnetic field due to the core to substantially zero; and
    a receiving coil configured to receive a signal resulting from precession of the nuclear spins about the direction of the earth's magnetic field, the precession resulting from the reduction of the magnetic field due to the core.

10. The apparatus of claim 9 further comprising an auxiliary coil configured to substantially eliminate a remainder of the static magnetic field in the earth formation.

11. The apparatus of claim 9 further comprising an additional coil configured to spoil a signal from a fluid in the borehole, the additional coil configured to generate a substantially multi-pole type magnetic field with fast spatial attenuation.

12. The apparatus of claim 9 wherein the magnetic core is made of a permeable magnetic material having a magnetic property related to a dimension of the magnetic core.

13. The apparatus of claim 9 wherein the magnetic core is made of a permeable magnetic material having a substantially rectangular magnetic hysteresis loop in a direction of residual magnetization.

14. The apparatus of claim 9 wherein the receiving coil includes a multi-turn receiving coil and the polarizing coil comprises a substantially small number of turns.

15. The apparatus claim 13 wherein the permeable magnetic material is selected from the group consisting of (i) a ferrite, (ii) an electrically conductive crystalline magnetic metal ribbons, (iii) an electrically conductive crystalline tape, (iv) an magnetic amorphous ribbon, and (v) an amorphous tape.

16. A method for measuring a nuclear magnetic resonance property in a region of interest of an earth formation; the method comprising:

producing a static magnetic field which polarizes nuclear spins in the region of interest using a source of switchable magnetic field, the source comprising a magnetic core having a controllable residual magnetization; and inducing and detecting a signal indicative of the nuclear magnetic resonance property;

wherein inducing the signal further comprises
(i) simultaneously switching off the static magnetic field and applying a pulsed magnetic field to provide adiabatic deviation of polarization direction of the nuclei from direction of the switchable static magnetic field,
(ii) reapplying the static magnetic field, and
(iii) periodically reversing the polarity of the switchable static magnetic field to generate gradient spin echoes.

17. The method of claim 16 wherein inducing the signal further comprises switching off the static magnetic field and generating precession of the nuclear spins around the earth's magnetic field.

18. The method of claim 17 further comprising using an auxiliary static magnetic field in order to correct for a residual inhomogeneous magnetic field remaining after switching off the static magnetic field.

19. The method of claim 17 further comprising generating an additional static magnetic field to spoil the signal from borehole fluids, said additional static magnetic field is a substantially multi-pole type magnetic field with fast spatial attenuation.

* * * * *